United States Patent
Thil et al.

(12) 
(10) Patent No.: US 6,437,170 B1
(45) Date of Patent: Aug. 20, 2002

(54) MIXTURE OF DIESTERS OF ADIPIC OR PHTHALIC ACID WITH ISOMERS OF NONANOLS

(75) Inventors: Lucien Thil; Boris Breitscheidel, both of Limburgerhof; Walter Disteldorf, Wachenheim; Edgar Zeller, Mannheim; Marc Walter, Frankenthal; Bernd Morsbach, Ludwigshafen; Knut Dornik, Schifferstadt, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/449,395

(22) Filed: Nov. 26, 1999

(30) Foreign Application Priority Data

Apr. 21, 1999 (DE) .......................................... 199 18 051
May 27, 1999 (DE) .......................................... 199 24 339

(51) Int. Cl.⁷ ............................................... C07C 69/76
(52) U.S. Cl. .......................... 560/76; 585/531; 560/204
(58) Field of Search ................... 560/76, 204; 585/531

(56) References Cited

U.S. PATENT DOCUMENTS

| | | | |
|---|---|---|---|
| 4,291,127 A | * | 9/1981 | Akabayashi et al. |
| 4,623,748 A | * | 11/1986 | Johnson et al. |
| 5,189,105 A | | 2/1993 | Miyazawa et al. |
| 5,849,972 A | * | 12/1998 | Vicari et al. |

FOREIGN PATENT DOCUMENTS

| | | | |
|---|---|---|---|
| GB | 1114379 | | 5/1968 |
| GB | 1330112 | * | 9/1973 |
| WO | WO 92/13818 | * | 8/1992 |
| WO | 92/13818 | | 8/1992 |
| WO | WOI92/13818 | * | 8/1992 |

* cited by examiner

*Primary Examiner*—Paul J. Killos
*Assistant Examiner*—Hector M Reyes
(74) *Attorney, Agent, or Firm*—Keil & Weinkauf

(57) ABSTRACT

The mixture described is a mixture of isomeric nonanol diesters of a dicarboxylic acid, selected from the class consisting of a mixture of diesters of adipic acid in the ¹H NMR spectrum of which, observed in $CDCl_3$, the ratio of the area under the resonance signals at chemical shifts in the range from 1.0 to 2.0 ppm with respect to TMS to the area under the resonance signals at chemical shifts in the range from 0.5 to 1.0 ppm with respect to TMS is from 1.20 to 5.00 and a mixture of diesters of phthalic acid, in the ¹H NMR spectrum of which, observed in $CDCl_3$, the ratio of the area under the resonance signals at chemical shifts in the range from 1.1 to 3.0 ppm with respect to TMS to the area under the resonance signals at chemical shifts in the range from 0.5 to 1.1 ppm with respect to TMS is from 1.00 to 4.00.

The diesters of adipic and phthalic acid are suitable as plasticizers for PVC-based molding compositions and have high compatibility, a low cold crack temperature, low torsional rigidity and/or high thermal stability.

11 Claims, No Drawings

MIXTURE OF DIESTERS OF ADIPIC OR PHTHALIC ACID WITH ISOMERS OF NONANOLS

The present invention relates to a mixture of isomeric nonanol diesters of adipic or phthalic acid. The alcohol component of these diesters is formed from an isomeric nonanols mixture.

Long-chain alcohols, e.g. $C_8$, $C_9$ and $C_{10}$ alcohols, are widely used for producing plasticizers. For this, the alcohols are reacted with polycarboxylic acids, such as phthalic acid or adipic acid, forming the corresponding esters. Commercially important representatives include adipates of $C_8$, $C_9$ and $C_{10}$ alcohols, for example di(2-ethylhexyl) adipate, diisononyl adipates and diisodecyl adipates, and phthalates of $C_8$, $C_9$ and $C_{10}$ alcohols, such as di(2-ethylhexyl) phthalate, diisononyl phthalates and diisodecyl phthalates.

Diisononyl adipates are used especially in films, profiles, synthetic leather, cables, lines or piping based on plasticized PVC. Diisononyl adipates are used in particular when the products are intended to be used at low temperatures.

Diisononyl phthalates are used especially in films, coatings and floorcoverings based on plasticized PVC. They are also used for producing PVC cable sheathing, for applications which include some at relatively high temperatures.

DE-A-20 09 505 discloses the use of isononanols in the form of bisisononyl esters of phthalic acid or adipic acid as plasticizers where the isononanols have been prepared from 2-ethyl-1-hexene in a known manner by the oxo synthesis, by reaction with carbon monoxide and hydrogen at elevated temperature and pressure in the presence of carbonyl complexes of metals of the 8th transition group of the Periodic Table, if desired followed by hydrogenation. The 2-ethyl-1-hexene is obtainable by dimerizing 1-butene with trialkyl aluminum compounds. The bisisononyl esters described are said to be suitable plasticizers for polyvinyl chloride and to have low volatility, low viscosity and to give good low-temperature resistance in the polyvinyl chloride compositions plasticized therewith.

U.S. Pat. No. 4,623,748 describes dialkyl adipates, inter alia diisononyl adipates, prepared by reacting propylene oligomers or butylene oligomers from the dimersol process in the presence of supported tantalum(V) halides/oxides as catalysts, reacting the resultant $C_8$, $C_9$ or $C_{12}$ olefins to give $C_9$, $C_{10}$ or, respectively, $C_{13}$ alcohols and esterifying these alcohols with adipic acid. The dialkyl adipates are said to have high flash points and to be suitable for use as lubricants.

GB 1,114,379 discloses an isomeric nonanols mixture which comprises n-nonanol and includes essentially no alcohols having more than one branch in their carbon skeleton. The mixture is prepared by hydroformylating an octene fraction obtained by polymerizing ethylene with catalysis by trialkylaluminum compounds, and then reducing the hydroformylation product.

WO 92/13818 describes the preparation of diisononyl phthalates starting from butenes and, where appropriate, from olefin mixtures comprising propene, via oligomerization on supported phosphoric acid catalysts at reaction temperatures of from 200 to 235° C. to give essentially octene-containing olefin mixtures, hydroformylation of these octene-containing olefin mixtures and subsequent hydrogenation to give essentially alcohol mixtures comprising isononanols, and esterification of these isononanol-containing alcohol mixtures using phthalic anhydride. The ester mixtures essentially comprising diisononyl phthalates are intended to be suitable as plasticizers for PVC.

DE 28 55 421 describes phthalates of $C_9$ alcohols, obtained by an oxo reaction of $C_8$ olefins, hydrogenation of the reaction product and esterification of the $C_9$ alcohols using phthalic anhydride, where from 3 to 20% of the $C_8$ olefins have an isobutane skeleton in each molecular chain and less than 3% of the olefins have quaternary carbon, and also more than 90% of the total amount of the $C_9$ olefins are present in the form of n-octenes, monomethylheptenes and dimethylhexenes. The $C_9$ phthalates are intended to be suitable as plasticizers for PVC.

EP 0 278 407 describes a $C_9$ alcohol mixture for plasticizers which comprises certain proportions of components with a specified GC retention behavior in relation to certain reference compounds. Plasticizers based on the $C_9$ alcohol mixture are intended to give advantageous resistance to low temperatures and good electrical insulation properties.

In using diisononyl esters as plasticizers in thermoplastic PVC-based molding compositions it is important that the resultant plasticized PVC compounds have both very high thermal stability and very good low-temperature flexibility properties. It is also important that there is little or no bleed-out of the plasticizers when they are used in the plasticized PVC compound. Neither the diisononyl esters described in the patent literature mentioned above nor commercially available plasticizers based on diisononyl esters comply with this combination of properties in an ideal manner.

It is an object of the present invention, therefore, to provide a mixture of isomeric nonanol diesters of a dicarboxylic acid, such that when the mixture is used as a plasticizer in PVC-based molding compositions, it gives good low-temperature flexibility properties and preferably high thermal stability of the molding compositions and preferably high compatibility.

We have found that this object is achieved by a mixture of isomeric nonanol diesters of a dicarboxylic acid selected from a mixture of diesters of adipic acid in the $^1$H NMR spectrum of which, observed in $CDCl_3$, the ratio of the area under the resonance signals at chemical shifts in the range from 1.0 to 2.0 ppm with respect to TMS to the area under the resonance signals at chemical shifts in the range from 0.5 to 1.0 ppm with respect to TMS is from 1.20 to 5.00, and a mixture of isomeric nonanol diesters of phthalic acid in the $^1$H NMR spectrum of which, taken up in $CDCl_3$, the ratio of the area under the resonance signals at chemical shifts in the range from 1.1 to 3.0 ppm with respect to TMS to the area under the resonance signals at chemical shifts in the range from 0.5 to 1.1 ppm with respect to TMS is from 1.00 to 4.00.

The isomeric nonanol diesters of adipic acid are also referred to as "diisononyl adipates" below and the isomeric nonanol diesters of phthalic acid are also referred to below as "diisononyl phthalates", or both may be referred to simply as "diesters".

The properties of the diisononyl adipates and the diisononyl phthalates and, respectively, their effect on the properties of their resultant plasticized molding compositions, are determined by the molecular structure, in particular by the structure of the isononyl groups of the alcohol component. It has been found that advantageous low-temperature flexibility properties and, at the same time, high compatibility are obtained if the isononyl groups of the alcohol component in the plasticizer have a particular ratio of methylene ($CH_2$) and methylidene (CH) groups to methyl ($CH_3$) groups. To distinguish the groups adequately from one another $^1$H NMR spectroscopy may be used.

The diisononyl adipates or phthalates according to the invention have a specific ratio of methylene groups and methylidene groups to methyl groups in the isononyl radical. For the purposes of the present invention, this ratio is determined with the aid of $^1$H NMR spectroscopy on a solution of the diisononyl adipates or phthalates in deuterochloroform (CDCl$_3$). The spectra are observed by, for example, dissolving 100 mg of substance in 5 ml of CDCl$_3$ and placing the solution in an NMR sample tube of diameter 5 mm. The equipment used for the NMR spectroscopy in the present studies was of "DPX-400" type from Bruker. The spectra were observed with a delay of 1 second, 32 scans, a pulse length of 3.7 μs and a sweep width of 8278.146 Hz. The resonance signals are indicated in terms of the chemical shift with respect to tetramethylsilane (TMS) as internal standard. Comparable results are obtained using other commercially available NMR equipment with the same operating parameters.

In the $^1$H NMR spectra obtained for the diisononyl adipates, among the resonance signals, the signals of the methyl groups of the isononyl groups with chemical shifts of from 0.5 to 1.0 ppm can be distinguished from the signals of all of the methylene groups and methylidene groups of the isononyl groups and of the adipic acid unit (internal methylene groups) with chemical shifts of from 1.0 to 2.0 ppm. The measurements are quantified by determining the area under the respective resonance signals, i.e. determining the area enclosed by the signal and the base line. Commercially available NMR equipment has devices for integrating the signal areas. The value of the integral of the signals assigned to the methylene groups and methylidene groups in the range from 1.0 to 2.0 ppm is then divided by the value of the integral of the signals assigned to the methyl groups in the range from 0.5 to 1.0 ppm, thus giving an intensity ratio which describes quantitatively the number of methylene groups and methylidene groups in the isononyl radical and in the adipic acid unit in relation to the number of methyl groups in the isononyl radical.

In the diisononyl adipates according to the invention this intensity ratio is greater than 1.20, preferably greater than 1.60, particularly preferably greater than 1.70. The intensity ratio is less than 5.00, in particular less than 2.30, particularly preferably less than 2.00. The ratio is preferably from 1.60 to 2.30 and in particular from 1.70 to 2.00.

In the $^1$H NMR spectra obtained for the diisononyl phthalates, among the resonance signals of the isononyl groups, the signals of the methyl groups with chemical shifts of from 0.5 to 1.1 ppm can be distinguished from the signals of the methylene groups and methylidene groups with chemical shifts of from 1.1 to 3.0 ppm. The measurements are quantified by determining the area under the respective resonance signals, as described. The value of the integral of the signals assigned to the methylene groups and methylidene groups in the range from 1.1 to 3.0 ppm is then divided by the value of the integral of the signals assigned to the methyl groups in the range from 0.5 to 1.1 ppm, thus giving an intensity ratio which describes quantitatively the number of methylene groups and methylidene groups in the isononyl radical in relation to the number of methyl groups.

In the case of the diisononyl phthalates according to the invention this intensity ratio is greater than 1.00, preferably greater than 1.50, particularly preferably greater than 1.55. The intensity ratio is less than 4.00, in particular less than 2.00, particularly preferably less than 1.80. The ratio is preferably from 1.50 to 2.00.

For the diisononyl phthalates according to the invention it is moreover possible to detect a triplet signal in the range from 0.7 to 0.8 ppm within the signals to be assigned to the methyl groups at from 0.8 to 1.1 ppm. The ratio calculated from the value of the integral from the signal areas of the remaining signals in the methyl-group range, i.e. at from 0.8 to 1.1 ppm, and the value of the integral from the signal area of the triplet signal at from 0.7 to 0.8 ppm here is at least 20.0, preferably at least 25.0. It is preferably not more than 200, in particular not more than 100.

The ester mixtures according to the invention are obtainable in a multistage process starting from a hydrocarbon mixture comprising butenes. In a first step, the butenes are dimerized to give a mixture of isomeric octenes. The octene mixture is then hydroformylated to give C$_9$ aldehydes and then hydrogenated to give isononanols, which are then converted into the adipates or phthalates. The preparation of diisononyl adipates or phthalates by the sequence of synthesis steps mentioned is known per se. However, an ester mixture satisfying the above definition is obtained only if, at least during the butene dimerization, preferably during the butene dimerization and the hydroformylation, specific defined parameters are complied with.

It is preferable, therefore, that the isomeric octenes mixture is obtained by bringing a hydrocarbon mixture comprising butenes into contact with a heterogeneous catalyst comprising nickel oxide. The isobutene content of the hydrocarbon mixture is preferably 5% by weight or less, in particular 3% by weight or less, particularly preferably 2% by weight or less, and most preferably 1.5% by weight or less, based in each case on the total butene content. A suitable hydrocarbon stream is that known as the C$_4$ cut, a mixture of butenes and butanes, available in large quantities from FCC plants or from steam crackers. A starting material used with particular preference is that known as raffinate II, which is an isobutene-depleted C$_4$ cut.

A preferred starting material comprises from 50 to 100% by weight, preferably from 80 to 95% by weight, of butenes and from 0 to 50% by weight, preferably from 5 to 20% by weight, of butanes. The following makeup of the butene fraction is given as a general guide to quantities:

1-butene from 1 to 99% by weight,
cis-2-butene from 1 to 50% by weight,
trans-2-butene from 1 to 99% by weight, and
isobutene up to 3% by weight.

Possible catalysts are catalysts known per se and comprising nickel oxide, as described, for example, by O'Connor et al. in Catalysis Today, 6, (1990) p. 329. Supported nickel oxide catalysts may be used, and possible support materials are silica, alumina, aluminosilicates, aluminosilicates having a layer structure and zeolites. Particularly suitable catalysts are precipitation catalysts obtainable by mixing aqueous solutions of nickel salts and of silicates, e.g. of sodium silicate and sodium nitrate, and, where appropriate, of other constituents, such as aluminum salts, e.g. aluminum nitrate, and calcining.

Particular preference is given to catalysts which essentially consist of NiO, SiO$_2$, TiO$_2$ and/or ZrO$_2$, and also, where appropriate, Al$_2$O$_3$. A most preferred catalyst comprises, as significant active constituents, from 10 to 70% by weight of nickel oxide, from 5 to 30% by weight of titanium dioxide and/or zirconium dioxide and from 0 to 20% by weight of aluminum oxide, the remainder being silicon dioxide. A catalyst of this type is obtainable by precipitating the catalyst composition at pH from 5 to 9 by adding an aqueous solution comprising nickel nitrate to an aqueous alkali solution which comprises titanium dioxide and/or zirconium dioxide, filtering, drying and annealing at from 350 to 650° C. For details of preparation of these catalysts reference may be made to DE-4 339 713. The entire content of the disclosure of that publication is incorporated herein by way of reference.

The hydrocarbon mixture comprising butenes is brought into contact with the catalyst, preferably at temperatures of from 30 to 280° C., in particular from 30 to 140° C. and particularly preferably from 40 to 130° C. This preferably takes place at a pressure of from 10 to 300 bar, in particular from 15 to 100 bar and particularly preferably from 20 to 80 bar. The pressure here is usefully set in such a way that the olefin-rich hydrocarbon mixture is liquid or in the supercritical state at the temperature selected.

Examples of reactors suitable for bringing the hydrocarbon mixture into contact with the heterogeneous catalyst are tube-bundle reactors and shaft furnaces. Shaft furnaces are preferred because the capital expenditure costs are lower. The dimerization may be carried out in a single reactor, where the oligomerization catalyst may have been arranged in one or more fixed beds. Another way is to use a reactor cascade composed of two or more, preferably two, reactors arranged in series, where the butene dimerization in the reaction mixture is driven to only partial conversion on passing through the reactor(s) preceding the last reactor of the cascade, and the desired final conversion is not achieved until the reaction mixture passes through the last reactor of the cascade. The butene dimerization preferably takes place in an adiabatic reactor or in an adiabatic reactor cascade.

After leaving the reactor or, respectively, the last reactor of a cascade, the octenes formed and, where appropriate, higher oligomers, are separated off from the unconverted butenes and butanes in the reactor discharge. The oligomers formed may be purified in a subsequent vacuum fractionation step, giving a pure octene fraction. During the butene dimerization, small amounts of dodenes are generally also obtained. These are preferably separated off from the octenes prior to the subsequent reaction.

In a preferred embodiment, some or all of the reactor discharge, freed from the oligomers formed and essentially consisting of unconverted butenes and butanes, is returned. It is preferable to select a return ratio such that the concentration of oligomers in the reaction mixture does not exceed 35% by weight, preferably 20% by weight, based on the hydrocarbon mixture of the reaction. This measure increases the selectivity of the butene dimerization in relation to those octenes which, after hydroformylation, hydrogenation and esterification, give particularly preferred diisononyl adipates and phthalates.

The octenes obtained are converted, in the second process step, by hydroformylation using synthesis gas in a manner known per se, into aldehydes having one additional carbon atom. The hydroformylation of olefins to prepare aldehydes is known per se and is described, for example, in J. Falbe, ed.: New Synthesis with Carbon monoxide, Springer, Berlin, 1980. The hydroformylation takes place in the presence of catalysts homogeneously dissolved in the reaction medium. The catalysts generally used here are compounds or complexes of metals of transition group VIII, specifically Co, Rh, Ir, Pd, Pt or Ru compounds, or complexes of these metals, either unmodified or modified, for example, using amine-containing or phosphine-containing compounds.

For the purposes of the present invention, the hydroformylation preferably takes place in the presence of a cobalt catalyst. It preferably takes place at from 120 to 240° C., in particular from 160 to 200° C., and under a synthesis gas pressure of from 150 to 400 bar, in particular from 250 to 350 bar. The hydroformylation preferably takes place in the presence of water. The ratio of hydrogen to carbon monoxide in the synthesis gas mixture used is preferably in the range from 70:30 to 50:50, in particular from 65:35 to 55:45.

The cobalt-catalyzed hydroformylation process may be carried out as a multistage process which comprises 4 stages: the preparation of the catalyst (precarbonylation), the catalyst extraction, the olefin hydroformylation and the removal of the catalyst from the reaction product (decobaltization). In the first stage of the process, the precarbonylation, an aqueous cobalt salt solution, e.g. cobalt formate or cobalt acetate, as starting material is reacted with carbon monoxide and hydrogen to prepare the catalyst complex ($HCo(CO)_4$) needed for the hydroformylation. In the second stage of the process, the catalyst extraction, the cobalt catalyst prepared in the first stage of the process is extracted from the aqueous phase using an organic phase, preferably using the olefin to be hydroformylated. Besides the olefin, it is occasionally advantageous to use the reaction products and byproducts of the hydroformylation for catalyst extraction, as long as these are insoluble in water and liquid under the reaction conditions selected. After the phase separation, the organic phase loaded with the cobalt catalyst is fed to the third stage of the process, the hydroformylation. In the fourth stage of the process, the decobaltization, the organic phase of the reactor discharge is freed from the cobalt carbonyl complexes in the presence of process water which may comprise formic acid or acetic acid, by treatment with oxygen or air. During this, the cobalt catalyst is destroyed by oxidation and the resultant cobalt salts are extracted back into the aqueous phase. The aqueous cobalt salt solution obtained from the decobaltization is returned to the first stage of the process, the precarbonylation. The raw hydroformylation product obtained may be fed directly to the hydrogenation. Another way is to extract a $C_9$ fraction from this in a usual manner, e.g. by distillation, and feed this to the hydrogenation.

The formation of the cobalt catalyst, the extraction of the cobalt catalyst into the organic phase and the hydroformylation of the olefins can also be carried out in a single-stage process in the hydroformylation reactor.

Examples of cobalt compounds which can be used are cobalt(II) chloride, cobalt(II) nitrate, the amine complexes or hydrate complexes of these, cobalt carboxylates, such as cobalt formate, cobalt acetate, cobalt ethyl hexanoate and cobalt naphthanoate, and also the cobalt caprolactamate complex. Under the conditions of the hydroformylation, the catalytically active cobalt compounds, specifically cobalt carbonyls, form in situ. It is also possible to use the carbonyl complexes of cobalt such as dicobalt octacarbonyl, tetracobalt dodecacarbonyl and hexacobalt hexadecacarbonyl.

The aldehyde mixture obtained during the hydroformylation is reduced to give primary alcohols. A partial reduction generally takes place straight away under the conditions of the hydroformylation, and it is also possible to control the hydroformylation in such a way as to give essentially complete reduction. However, the hydroformylation product obtained is generally hydrogenated in a further process step using hydrogen gas or a hydrogen-containing gas mixture. The hydrogenation generally takes place in the presence of a heterogeneous hydrogenation catalyst. The hydrogenation catalyst used may comprise any desired catalyst suitable for hydrogenating aldehydes to give primary alcohols. Examples of suitable commercially available catalysts are copper chromite, cobalt, cobalt compounds, nickel, nickel compounds, which, where appropriate, comprise small amounts of chromium or of other promoters, and mixtures of copper, nickel and/or chromium. The nickel compounds are generally in a form supported on support materials, such as alumina or kieselguhr. It is also possible to use catalysts comprising noble metals, such as platinum or palladium.

A suitable method of carrying out the hydrogenation is a trickle-flow method, where the mixture to be hydrogenated and the hydrogen gas or, respectively, the hydrogen-containing gas mixture are passed, for example cocurrently, over a fixed bed of the hydrogenation catalyst.

The hydrogenation preferably takes place at from 50 to 250° C., in particular from 100 to 150° C., and at a hydrogen pressure of from 50 to 350 bar, in particular from 150 to 300 bar. The desired isononanol fraction in the reaction discharge obtained during the hydrogenation can be separated off by fractional distillation from the $C_8$ hydrocarbons and higher-boiling products.

In a further process step, the isononanols are then converted in a manner known per se into the isomeric nonanol diesters of adipic or phthalic acid, by esterification with adipic or phthalic acid or with a derivative thereof. The phthalates according to the invention are preferably prepared using phthalic anhydride. The isomeric nonanols mixture described above is preferably reacted in excess with the particular dicarboxylic acid or the derivative thereof, in particular in a molar excess of 5 to 30%, preferably in the presence of an acylation catalyst, such as a dialkyl titanate, e.g. isopropyl butyl titanate, or of an acid, such as methanesulfonic acid or sulfuric acid.

The reaction with the dicarboxylic acid or with a dicarboxylic acid derivative generally takes place at temperatures of from 150 to 300° C., preferably from 200 to 250° C. In an appropriate embodiment, an inert gas, such as nitrogen, is bubbled into the reaction mixture during the reaction and the water formed in the reaction is removed progressively from the reaction mixture by the inert gas stream. Once the reaction has ended, the novel mixture of isomeric nonanol diesters of adipic or phthalic acid is isolated from the reaction mixture, by, for example, distilling off the isononanol excess in vacuo, neutralizing the crude diester with an aqueous alkali, such as aqueous sodium hydroxide, forming a two-phase mixture, separating off the aqueous phase and washing the organic phase. For further purification, the neutralized and washed diester is preferably stripped using steam at elevated temperature in vacuo. The purified diester may then be dried at elevated temperature in vacuo by passing a nitrogen stream through the mixture, and, if desired, further purified by being brought into contact with an adsorbant, such as activated carbon or bleaching earth.

The diisononyl adipates according to the invention prepared in this way have a density of from 0.900 to 0.940 g/cm$^3$, preferably from 0.910 to 0.930 g/cm$^3$, in particular from 0.918 to 0.922 g/cm$^3$, a viscosity of from 15.0 to 25.0 mPa.s, preferably from 16.0 to 22.0 mPa.s, particularly preferably from 17.0 to 20.0 mPa.s, and a refractive index $n_D^{20}$ of from 1.445 to 1.455, preferably from 1.447 to 1.453, particularly preferably from 1.448 to 1.452.

The diisononyl phthalates according to the invention prepared in this way generally have a density of from 0.950 to 0.990 g/cm$^3$, preferably from 0.960 to 0.980 g/cm$^3$, in particular from 0.967 to 0.973 g/cm$^3$, a viscosity of from 60.0 to 110.0 mPas, preferably from 63.0 to 80.0 mPas, in particular from 65.0 to 75.0 mPas, and a refractive index $n_D^{20}$ of from 1.470 to 1.495, preferably from 1.476 to 1.490, in particular from 1.480 to 1.486.

The novel mixtures of diesters are preferably suitable as plasticizers for preparing thermoplastic molding compositions, in particular for PVC-based molding compositions.

The diisononyl adipates according to the invention are particularly suitable here for preparing plasticized PVC compounds which have very good low-temperature flexibility properties together with high plasticizer compatibility. The diisononyl phthalates according to the invention are particularly suitable for preparing plasticized PVC compounds which have high thermal stability together with very good low-temperature flexibility properties.

The following method is preferably used to prepare and investigate the plasticized PVC compounds prepared using the novel diesters:

A mixture is prepared from PVC powder, preferably PVC powder prepared by the suspension process, the novel diester as plasticizer and, where appropriate, other additives, such as stabilizers, lubricants, fillers, pigments, dyes, flame retardants, light stabilizers, antistats, blowing agents or biostabilizers. This mixture is then plastified on mixing rolls and milled to give a milled sheet. The milled sheet is then molded under pressure to give a plasticized PVC film, on which the performance tests are then carried out.

Low-temperature flexibility properties of plasticized PVC compounds are preferably characterized with the aid of the cold crack temperature. This is the temperature at which a plasticized PVC compound, when cold, begins to exhibit visible damage when subjected to mechanical loading. The cold crack temperature is determined in accordance with DIN 53372. Another criterion for characterizing low-temperature flexibility properties is "torsional rigidity". For the purposes of the present invention, torsional ridigity is the temperature at which a plasticized PVC compound can be twisted through a certain angle when a defined force is applied. The torsional ridigity is determined to DIN 53447.

The thermal stability of the plasticized PVC compounds is preferably characterized with the aid of what is known as HCl residual stability. This is the period of time for which the plasticized PVC compound at 200° C. continues to show no decomposition with HCl cleavage. HCl residue stability is determined in accordance with the VDE Standard 0472, §614.

The compatibility of a plasticizer in a plasticized PVC compound is determined by storing the plasticized PVC compound at 70° C. and 100% relative humidity for a prolonged period and determining, by weighing after particular intervals, the weight loss of the plasticized PVC compound as a result of bleed-out of the plasticizer. The operating specification for studying compatibility is as follows:

Purpose of the Study

The test gives a quantitative measurement of the compatibility of plasticizers in plasticized PVC mixing specifications. It is carried out at elevated temperature (70° C.) and humidity (100% rel. H.). The data obtained are evaluated as a function of the storage time.

Test Specimens

The test specimens (sheets) used have dimensions of 75×110×0.5 mm. The sheets are punched on their face sides and inscribed (soldering iron) and weighed.

Test Equipment

Heraeus drying cabinet at 70° C., analysis balance, Testotherm thermometer with sensor for interior measurement within the drying cabinet.

Method

The temperature in the interior of the drying cabinet is set to 70° C. The prepared weighed films are suspended on a wire rack and placed in a glass tank filled to a height of about 5 cm with water (deionized water). Care should be taken that the sheets do not touch one another. The lower edges of the sheets must not pass into the water. The glass tank is sealed with a PE film so as to be steamtight, so that the steam subsequently produced within the glass tank cannot escape. The level of water in the glass reservoir is checked daily and any water lost is replaced.

Storage Time

Each day, two sheets are removed from the glass tank and conditioned for one hour by free suspension in the atmosphere. The surfaces of the sheets are then cleaned with methanol. The sheets are then dried while freely suspended for 16 h at 70° C. in a drying cabinet with forced convection. After removal from the drying cabinet, the sheets are conditioned by free suspension for one hour, and then weighed. The data given are in each case the arithmetic mean of the weight losses of the sheets.

The invention is described in greater detail using the examples below:

EXAMPLE 1

Preparation of a Novel Diisononyl Adipate

Process Step 1 (Butene Dimerization)

The butene dimerization was carried out continuously in an adiabatic reactor, composed of two subreactors (length: in each case 4 m, diameter: in each case 80 cm) with intermediate cooling at 30 bar. The starting product used was a raffinate II with the following makeup:

| | |
|---|---|
| isobutane | 2% by weight |
| n-butane | 10% by weight |
| isobutene | 2% by weight |
| 1-butene | 32% by weight |
| trans-2-butene | 37% by weight and |
| cis-2-butene | 17% by weight. |

The catalyst used was a material in accordance with DE 4 339 713, composed of 50% by weight of NiO, 12.5% by weight of $TiO_2$, 33.5% by weight of $SiO_2$ and 4% by weight of $Al_2O_3$, in the form of 5×5 mm tablets. The reaction was carried out with a throughput of 0.375 kg of raffinate II per l of catalyst and hour, with return of the reactor discharge freed from the oligomers formed, with a return ratio of unreacted $C_4$ hydrocarbons to fresh raffinate II of 3, an inlet temperature at the first subreactor of 38° C. and an inlet temperature at the second subreactor of 60° C. The conversion, based on the butenes present in the raffinate II, was 83.1%, and the selectivity for the desired octenes was 83.3%. Fractional distillation of the reactor discharge was used to separate off the octene fraction from unreacted raffinate II and the high-boilers.

Process Step 2 (Hydroformylation Followed by Hydrogenation)

750 g of the octene mixture prepared in process step 1 were reacted for 5 hours discontinuously, in an autoclave, with 0.13% by weight of dicobalt octacarbonyl $Co_2(CO)_8$ as catalyst, with addition of 75 g of water, at 185° C. and with a synthesis gas pressure of 280 bar at a ratio of $H_2$ to CO in the mixture of 60/40. Further material was injected to make up for the consumption of synthesis gas, seen in a fall-off of pressure in the autoclave. After releasing the pressure in the autoclave, the reaction discharge, with 10% strength by weight acetic acid, was freed oxidatively from the cobalt catalyst by introducing air, and the organic product phase was hydrogenated using Raney nickel at 125° C. and with a hydrogen pressure of 280 bar for 10 h. The isononanol fraction was separated off from the $C_8$ paraffins and the high-boilers by fractional distillation of the reaction discharge.

Process Step 3 (Esterification)

In the third process step, 865.74 g of the isononanol fraction obtained in process step 2 (20% molar excess based on adipic acid) were reacted with 365.25 g of adipic acid and 0.42 g of isopropyl butyl titanate catalyst in a 2 l autoclave into which nitrogen was bubbled (10 l/h) with a stirrer speed of 500 rpm and a reaction temperature of 230° C. The water formed in the reaction was removed progressively from the reaction mixture with the nitrogen stream. The reaction time was 180 min. The isononanol excess was then distilled off at a reduced pressure of 50 mbar. 1000 g of the crude diisononyl adipate were neutralized by stirring for 10 minutes at 80° C. with 150 ml of 0.5% strength aqueous sodium hydroxide. This gave a two-phase mixture with an upper organic phase and a lower aqueous phase (waste liquor with hydrolyzed catalyst). The aqueous phase was separated off, and the organic phase subjected to two further washings with 200 ml of $H_2O$. For further purification, the neutralized and washed diisononyl adipate was stripped using steam at 180° C. and a reduced pressure of 50 mbar for two hours. The purified diisononyl adipate was then dried for 30 min at 150° C./50 mbar by passing a nitrogen stream (2 l/h) through the material, then mixed with activated carbon for 5 min and filtered off with suction via a suction filter using Supra-Theorit 5 filtration aid (temperature 80° C.).

The resultant diisononyl adipate has a density of 0.920 $g/cm^3$, a viscosity of 19.2 mPa.s, a refractive index $n_D^{20}$ of 1.4500, an acid number of 0.03 mg KOH/g, a water content of 0.02% and a purity, measured by GC, of 99.86%.

Characterization of the Novel Diisononyl Adipate by $^1H$ NMR Spectroscopy

The value of the integral across the areas of the signal groups in the range of the methylene groups and methylidene groups (including the internal methylene groups of the adipic acid component) from 1.0 to 2.0 ppm is 576.32, and the value of the integral across the areas of the signal groups in the range of the methyl groups from 0.5 to 1.0 ppm is 329.47. The resultant intensity ratio is 576.32/329.47= 1.75.

Preparation and Testing of a Plasticized PVC Compound Using the Novel Diisononyl Adipate 150 g of "Vinoflex S 7114" suspension PVC, 75 g of the novel diisononyl adipate and 3 g of "Lankromark LZB 753" Ba/Zn stabilizer are mixed at room temperature using a hand mixer. The mixture is then plasticized on steam-heated laboratory mixing rolls (Collin, model "150") and processed to give a milled sheet. The temperature of each of the two rolls is 170° C., and the rotation rates are 15 rpm (front roll) and 12 rpm (rear roll), and the milling time is 5 minutes. This gives a milled sheet of thickness 0.55 mm. The cooled milled sheet is then molded with pressure at 180° C. and 220 bar for 400 s in a Collin model "400 P" press to give a plasticized PVC film of thickness 0.50 mm.

The cold crack temperature (in accordance with DIN 53372), the torsional rigidity (in accordance with DIN 53447) and the compatibility (in accordance with the operating specification given above) of this plasticized PVC film are then determined. The results are given in Table 1 together with the intensity ratio from the $^1H$ NMR spectrum.

Comparative Example 1

For comparison, a commercially available diisononyl adipate of "Exxon Jayflex DINA" type was studied by $^1H$ NMR spectroscopy, and using this diisononyl adipate a plasticized PVC compound was prepared and tested.

In the $^1$H NMR spectrum of Exxon Jayflex DINA the value for the integral across the areas of the signal groups in the range of the methylene groups and methylidene groups (including the internal methylene groups of the adipic acid component) from 1.0 to 2.0 ppm is 517.16, and the value of the integral across the areas of the signal groups in the range of the methyl groups from 0.5 to 1.0 ppm is 453.95. This gives an intensity ratio of 517.16/453.95=1.14.

As in Example 1, the commercially available diisononyl adipate Exxon Jayflex DINA was used to produce a plasticized PVC film, and the cold crack temperature (in accordance with DIN 53372), torsional rigidity (in accordance with DIN 53447) and compatibility (in accordance with the operating specification given above) were determined. The results are given in Table 1 together with the intensity ratio from the $^1$H NMR spectrum.

TABLE 1

| Diisononyl adipate | Example 1 | Comparative Example 1 "Exxon Jayflex DINA" |
|---|---|---|
| Intensity ratio of the signal groups at 1.0–2.0 ppm (CH$_2$ and CH groups) and 0.5–1.0 ppm (CH$_3$ groups) in $^1$H NMR spectrum | 1.75 | 1.14 |
| Cold crack temperature (° C.) of plasticized PVC compound | −64 | −56 |
| Torsional rigidity (° C.) of plasticized PVC compound | −55 | −49 |
| Compatibility test at 70° C. and 100% relative humidity Weight loss of plasticized PVC compound (% by wt.) | | |
| After 1 d | 0.11 | 0.22 |
| After 3 d | 0.27 | 0.33 |
| After 7 d | 0.57 | 0.69 |
| After 14 d | 0.80 | 0.88 |
| After 28 d | 1.00 | 1.07 |

The novel diisononyl adipate (Example 1) differs significantly from the diisononyl adipate available commercially in terms of the intensity ratio of the signal groups at from 1.0 to 2.0 ppm (CH$_2$ and CH groups) and from 0.5 to 1.0 ppm (CH$_3$ groups). The intensity ratio is 1.75 for the diisononyl adipate of Example 1, compared with 1.14 for Exxon Jayflex DINA.

The cold crack temperature of the plasticized PVC compound prepared using the novel diisononyl adipate of Example 1 is −64° C. and its torsional rigidity is −55° C., significantly lower values than for the compound prepared from Exxon Jayflex DINA (cold crack temperature −56° C., torsional rigidity −49° C.). The novel diisononyl adipate therefore gives plasticized PVC compounds with significantly better low-temperature flexibility properties than does Exxon Jayflex DINA.

The plasticized PVC compound prepared using the novel diisononyl adipate from Example 1 also has significantly better plasticizer compatibility than the compound prepared from Exxon Jayflex DINA. For example, for the compound in Example 1 the weight loss due to bleed-out of the plasticizer is only 0.57% by weight after 7 d, whereas the corresponding value for the compound of the comparative example is 0.68% by weight. This confirms that use of the novel diisononyl adipates gives plasticized PVC compounds having very good low-temperature flexibility properties together with very good compatibility of the plasticizer in the plasticized PVC compound.

EXAMPLE 2

Preparation of a Novel Diisonoyl [Sic] Phthalate

For the preparation, 865.74 g of the isononanol fraction obtained as in Example 1, process steps 1 and 2, were esterified with 370.30 g of phthalic anhydride (20% excess with respect to phthalic anhydride) and 0.42 g of isopropyl butyl titanate catalyst in a 2 l autoclave into which nitrogen was bubbled (10 l/h) with a stirrer speed of 500 rpm and a reaction temperature of 230° C. The water formed in the reaction was removed progressively from the reaction mixture with the nitrogen stream. The reaction time was 180 min. The isononanol excess was then distilled off at a reduced pressure of 50 mbar. 1000 g of the crude diisononyl phthalate were neutralized by stirring for 10 minutes at 80° C. with 150 ml of 0.5% strength aqueous sodium hydroxide. This gave a two-phase mixture with an upper organic phase and a lower aqueous phase (waste liquor with hydrolyzed catalyst). The aqueous phase was separated off, and the organic phase subjected to two further washings with 200 ml of H$_2$O. For further purification, the neutralized and washed diisononyl phthalate was stripped using steam at 180° C. and a reduced pressure of 50 mbar for 2 h. The purified diisononyl phthalate was then dried for 30 min at 150° C./50 mbar by passing a stream of nitrogen (2l/h) through the material, then mixed with activated carbon for 5 min and filtered off with suction via a suction filter using Supra-Theorit 5 filtration aid (temperature 80° C.).

The resultant diisononyl phthalate has a density of 0.973 g/cm$^3$, a viscosity of 73.0 mPas, a refractive index n$_D^{20}$ of 1.4853, an acid number of 0.03 mg KOH/g, a water content of 0.03% and a purity, measured by GC, of 99.83%.

Characterization of the Novel Diisononyl Phthalate by $^1$H NMR Spectroscopy

The $^1$H NMR spectrum of the diisononyl phthalate of Example 1 was observed using a Bruker model DPX-400 NMR apparatus. The value of the integral across the areas of the signal groups in the range of the methylene groups and methylidene groups, from 1.1 to 3.0 ppm, is 125.5, and the value of the integral across the areas of the signal groups in the range of the methyl groups, from 0.5 to 1.1 ppm, is 75.5. The resultant intensity ratio is 125.5/75.5=1.66.

At higher resolution, the signals in the methyl group range at from 0.8 to 1.1 ppm are seen, with a value of 1000 for the integral across the signal areas, and a triplet signal is seen at from 0.7 to 0.8 ppm with a value of 39.493 for the integral across the signal area. The resultant intensity ratio is 1000/39.493=25.3.

Preparation and Testing of a Plasticized PVC Compound Using the Novel Diisononyl Phthalate 150 g of Vinoflex S 7114 suspension PVC, 100 g of the novel diisononyl phthalate and 3 g of Lankromark LZB 753 Ba/Zn stabilizer are mixed at room temperature using a hand mixer. The mixture is then plastified on steam-heated laboratory mixing rolls (Collin, model 150) and processed to give a milled sheet. The temperature of the two rolls is in each case 170° C., and the rotation rates are 15 rpm (front roll) and 12 rpm (rear roll), and the milling time is 5 minutes. This gives a milled sheet of thickness 0.55 mm. The cooled milled sheet is then molded with pressure at 180° C. and with a pressure of 220 bar within 400 s on a Collin model 400 P press to give a plasticized PVC film of thickness 0.50 mm.

The HCl residual stability (in accordance with VDE Standard 0472, §614) and the cold crack temperature (in accordance with DIN 53372) of this plasticized PVC film are then determined. The results are given in Table 2 together with the intensity ratios from $^1$H NMR spectrum.

Comparative Examples 2 and 3

For comparison, two commercially available diisononyl phthalates, Exxon Jayflex DINP (Comparative Example 2) and BASF Palatinol DN (Comparative Example 3), were studied as above using $^1$H NMR spectroscopy, and plasticized PVC compounds prepared using these diisononyl phthalates were tested.

In the $^1$H NMR spectrum of Exxon Jayflex DINP the value of the integral across the areas of the signal groups in the range of the methylene groups and methylidene groups, from 1.1 to 3.0 ppm, is 95, and the value of the integral across the areas of the signal groups in the range of the methyl groups, from 0.5 to 1.1 ppm, is 106. This gives an intensity ratio of 95/106=0.90. No triplet signal could be detected in the range from 0.7 to 0.8 ppm.

In the $^1$H NMR spectrum of BASF Palatinol DN the value of the integral across the areas of the signal groups in the range of the methylene groups and methylidene groups, from 1.1 to 3.0 ppm, is 70, and the value of the integral across the areas of the signal groups in the range of the methyl groups, from 0.5 to 1.1 ppm, is 131.5. This gives an intensity ratio of 70/131.5=0.53. No triplet signal could be detected in the range from 0.7 to 0.8.

As in Example 2, the commercially available diisononyl phthalates Exxon Jayflex DINP and BASF Palatinol DN were used to produce plasticized PVC films, and the HCl residual stability (in accordance with VDE Standard 0472, §614) and the cold crack temperature (in accordance with DIN 53372) of these films were determined. The results are given in Table 2 together with the intensity ratios from the $^1$H NMR spectrum.

TABLE 2

| Diisononyl phthalate | Example 2 | Comparative Example 2 with Exxon Jayflex DINP | Comparative Example 3 with BASF Palatinol DN |
|---|---|---|---|
| Intensity ratio of the signal groups at 1.1–3.0 ppm (CH$_2$ and CH groups) and 0.5–1.1 ppm (CH$_3$ groups) in $^1$H NMR spectrum | 1.66 | 0.90 | 0.53 |
| Intensity ratio of signal groups at 0.8–1.1 ppm and the signal group (triplet) at 0.7–0.8 ppm in $^1$H NMR spectrum | 25.3 | — | — |
| Cold crack temperature (° C.) of the plasticized PVC compound | −42 | −31 | −23 |
| HCl residual stability at 200° C. (min) of the plasticized PVC compound | 18 | 13.8 | 14.4 |

It is clear from the data in Table 2 that the novel diisononyl phthalate (Example 2) differs significantly from the diisononyl phthalates available commercially in terms of the intensity ratio of the signal groups at from 1.1 to 3.0 ppm (CH$_2$ and CH groups) and from 0.5 to 1.1 ppm (CH$_3$ groups). The intensity ratio is 1.66 in Example 2, compared with 0.90 for Exxon Jayflex DINP and 0.53 for BASF Palatinol DN. The commercially available diisononyl phthalates moreover have no triplet signal at from 0.7 to 0.8 ppm in the $^1$H NMR spectrum.

The cold crack temperature of the plasticized PVC compound prepared using the novel diisononyl phthalate of Example 2 is −42° C., a value significantly lower than for the compounds prepared on the basis of Exxon Jayflex DINP and BASF Palatinol DN (Comparative Examples 2 and 3) (cold crack temperatures respectively −31 and −23° C.). The plasticized PVC compound prepared using the novel diisononyl phthalate of Example 2 also has an HCl residual stability of 18 min, a value significantly higher than that for compounds prepared from Exxon Jayflex DINP and BASF Palatinol DN (HCl residual stabilities respectively 13.8 and 14.4 min). This confirms that use of the novel diisononyl phthalates gives plasticized PVC compounds with higher thermal stability and at the same time very good low-temperature flexibility properties.

We claim:

1. A mixture of isomeric nonanol diesters of adipic acid in the $^1$H NMR spectrum of which, observed in CDCl$_3$, the ratio of the area under the resonance signals at chemical shifts in the range from 1.0 to 2.0 ppm with respect to TMS to the area under the resonance signals and chemical shifts in the range from 0.5 to 1.0 ppm with respect to TMS is from 1.20 to 5.00.

2. A mixture as claimed in claim 1, obtained by esterifying, with adipic acid or a derivative thereof, an isomeric nonanols mixture obtained by hydroformylating and hydrogenating an isomeric octenes mixture, where the isomeric octenes mixture is obtained by bringing a butene-containing hydrocarbon mixture into contact with a heterogeneous catalyst comprising nickel oxide.

3. A mixture as claimed in claim 2, wherein the hydrocarbon mixture comprises 5% by weight or less of isobutene, based on the total butene content.

4. A mixture as claimed in claim 2, wherein the hydrocarbon mixture comprises 3% by weight or less of isobutene, based on the total butene content.

5. A method for plasticizing a molding composition, comprising the step of combining the mixture of claim 1 with the molding composition.

6. A mixture of isomeric nonanols which
upon esterification with adipic acid yields a mixture of diesters of adipic acid in the $^1$H NMR spectrum of which, observed in DCDl$_3$, the ratio of the area under the resonance signals at chemical shifts in the range from 1.0 to 2.0 ppm with respect to TMS to the area under the resonance signals and chemical shifts in the range from 0.5 to 1.0 ppm with respect to TMS is from 1.20 to 5.00 and/or
upon esterification with phthalic acid yields a mixture of diesters of phthalic acid, in the $^1$H NMR spectrum of which, observed in CDCl$_3$, the ratio of the area under the resonance signals at chemical shifts in the range from 1.1 to 3.0 ppm with respect to TMS to the area under the resonance signals at chemical shifts in the range from 0.5 to 1.1 ppm with respect to TMS is from 1.00 to 4.00.

7. A mixture of isomeric nonanols, obtained by hydroformylating an isomeric octenes mixture in the presence of a cobalt catalyst and hydrogenating the hydroformylation product, where the isomeric octenes mixture is obtained by bringing a butene-containing hydrocarbon mixture which comprises 5% by weight or less of isobutene, based on the total butene content, into contact with a heterogeneous catalyst comprises, as significant active constituents, from 10 70% by weight of nickel oxide, from 5 to 30% by weight of titanium dioxide and/or zirconium dioxide and from 0 to 20% by weight of aluminum oxide, and the remainder is silicon dioxide.

8. A mixture of isomeric nonanol diesters of phthalic acid, in the $^1$H NMR spectrum of which, observed in CDCl$_3$, the ratio of the area under the resonance signals at chemical shifts in the range from 1.1 to 3.0 ppm with respect to TMS to the area under the resonance signals at chemical shifts in the range from 0.5 to 1.1 ppm with respect to TMS is from 1.00 to 4.00.

9. A mixture as claimed in claim 1, obtained by esterifying with phthalic acid or a derivative thereof, an isomeric nonanols mixture obtained by hydroformylating and hydrogenating an isomeric octenes mixture, where the isomeric octenes mixture is obtained by bringing a butene-containing hydrocarbon mixture into contact with a heterogeneous catalyst comprising nickel oxide.

10. A mixture as claimed in claim 9 wherein the hydrocarbon mixture comprises 5% by weight or less of isobutene, based on the total butene content.

11. A mixture as claimed in claim 9, wherein the hydrocarbon mixture comprises 3% by weight or less of isobutene, based on the total butene content.

* * * * *

UNITED STATES PATENT AND TRADEMARK OFFICE
CERTIFICATE OF CORRECTION

PATENT NO. : 6,437,170 B1
DATED : August 20, 2002
INVENTOR(S) : Thil et al.

It is certified that error appears in the above-identified patent and that said Letters Patent is hereby corrected as shown below:

Column 14,
Lines 22 and 47, "1.20" should be -- 1.60 --;
Line 25, after "hydroformylating" insert -- inthe presence of a cobalt catalyst --;
Line 29, "comprising nickel oxide" should be -- wherein the catalyst comprises, as significant active constituents, from 10 to 70% by weight of nickel oxide, from 5 to 30% by weight of titanium dioxide and/or zirconium dioxide and from 0 to 20% by weight of aluminum oxide, and the remainder is silicon dioxide --;
Line 64, "10 70%" should be -- 10 to 70% --.

Column 15,
Line 7, "1.20" should be -- 1.50 --;
Line 8, "1" should be -- 11 --;
Line 10, after "hydroformulating" insert -- in the presence of a cobalt catalyst --.

Column 16,
Line 3, "comprising nickel oxide" should be -- wherein the catalyst comprises, as significant active constituents, from 10 to 70% by weight of nickel oxide, from 5 to 30% by weight of titanium dioxide and/or zirconium dioxide and from 0 to 20% by weight of aluminum oxide, and the remainder is silicon dioxide --.

Signed and Sealed this

Eleventh Day of February, 2003

JAMES E. ROGAN
*Director of the United States Patent and Trademark Office*